(12) United States Patent
Malek (10) Patent No.: US 11,357,614 B1
(45) Date of Patent: Jun. 14, 2022

(54) BREAST IMPLANT

(71) Applicant: Marcel Malek, Scottsdale, AZ (US)

(72) Inventor: Marcel Malek, Scottsdale, AZ (US)

( * ) Notice: Subject to any disclaimer, the term of this patent is extended or adjusted under 35 U.S.C. 154(b) by 0 days.

(21) Appl. No.: 17/450,803

(22) Filed: Oct. 13, 2021

Related U.S. Application Data (60) Provisional application No. 63/209,397, filed on Jun. 11, 2021.

(51) Int. Cl.
*A61F 2/12* (2006.01)

(52) U.S. Cl.
CPC ........ *A61F 2/12* (2013.01); *A61F 2220/0008* (2013.01); *A61F 2250/0003* (2013.01)

(58) Field of Classification Search
CPC ................ A61F 2/12; A61F 2220/0008; A61F 2250/0003
USPC .......................................................... 623/7–8
See application file for complete search history.

(56) References Cited

U.S. PATENT DOCUMENTS

| | | | |
|---|---|---|---|
| 5,480,430 A | 1/1996 | Carlisle et al. | |
| 6,146,418 A * | 11/2000 | Berman ................ | A61M 31/00 623/7 |
| 6,605,116 B2 | 8/2003 | Falcon et al. | |
| 9,463,087 B2 * | 10/2016 | Hristov ...................... | A61F 2/12 |
| 9,700,405 B2 * | 7/2017 | Davila .................... | A61B 90/02 |
| 10,617,516 B2 * | 4/2020 | Davila ....................... | A61F 2/12 |
| 11,160,630 B2 * | 11/2021 | Schuessler ................ | A61F 2/12 |
| 2003/0205846 A1 | 11/2003 | Bellin et al. | |
| 2004/0127985 A1 * | 7/2004 | Bellin ..................... | B29C 41/14 623/8 |
| 2007/0135916 A1 | 6/2007 | Maxwell et al. | |
| 2009/0240342 A1 | 9/2009 | Lindh, Sr. et al. | |
| 2010/0178414 A1 | 7/2010 | Judge et al. | |
| 2012/0165934 A1 * | 6/2012 | Schuessler ................ | A61F 2/12 623/8 |
| 2013/0231743 A1 | 9/2013 | Becker | |
| 2014/0039617 A1 * | 2/2014 | Maxwell .................... | A61F 2/12 623/8 |
| 2015/0272722 A1 * | 10/2015 | Davila ....................... | A61F 2/12 623/8 |
| 2016/0082235 A1 * | 3/2016 | Mosharrafa ........... | A61M 29/02 606/192 |
| 2016/0228236 A1 * | 8/2016 | Egnelöv .................... | A61F 2/12 |
| 2016/0331513 A1 * | 11/2016 | Brown ...................... | A61F 2/12 |
| 2017/0224869 A1 | 8/2017 | Shah et al. | |
| 2019/0015194 A1 | 1/2019 | Bocca | |
| 2019/0142574 A1 * | 5/2019 | Quirós .................... | A61L 27/50 623/8 |
| 2020/0046489 A1 | 2/2020 | Feinberg et al. | |
| 2020/0100892 A1 * | 4/2020 | Limem .................. | A61L 27/18 |

(Continued)

FOREIGN PATENT DOCUMENTS

| | | |
|---|---|---|
| FR | 2826255 A1 | 12/2002 |
| WO | 1995001864 A1 | 1/1995 |

*Primary Examiner* — Suzette J Gherbi
(74) *Attorney, Agent, or Firm* — Adam R. Stephenson, Ltd.

(57) ABSTRACT

Implementations of a breast implant may include a shell including a posterior cephalic portion, a posterior caudal portion, an anterior cephalic portion, and an anterior caudal portion. Implementations of the breast implant may also include an anchor coupled within the shell and coupled directly and fixedly to the posterior caudal portion and the anterior caudal portion. The anchor may prevent rotation of the breast implant. The outer surface of the shell may be non-textured.

18 Claims, 8 Drawing Sheets

(56) References Cited

U.S. PATENT DOCUMENTS

2020/0345476 A1* 11/2020 Wang .................. A61F 2/12
2020/0397554 A1* 12/2020 Van Epps ............ A61F 2/12
2021/0346150 A1* 11/2021 Chacón Quirós ..... A61F 2/12

* cited by examiner

BREAST IMPLANT

CROSS REFERENCE TO RELATED APPLICATIONS

This document claims the benefit of the filing date of U.S. Provisional Patent Application 63/209,397, entitled "Breast Implant" to Marcel Malek which was filed on Jun. 11, 2021, the disclosure of which is hereby incorporated entirely herein by reference.

BACKGROUND

1. Technical Field

Aspects of this document relate generally to breast implants. More specific implementations involve breast implants having an anatomical shape.

2. Background

Breast implants are prosthesis used to change the shape and appearance of a breast. Breast implants may be used in reconstructive or aesthetic surgeries for individuals following a mastectomy, to correct congenital defects or other deformities of the chest wall, or for cosmetic reasons to enhance the appearance of a breast. Breast implants are filled with a fluid medium.

SUMMARY

Implementations of a breast implant may include a shell including a posterior cephalic portion, a posterior caudal portion, an anterior cephalic portion, and an anterior caudal portion. Implementations of the breast implant may also include an anchor coupled within the shell and coupled directly and fixedly to the posterior caudal portion and the anterior caudal portion. The anchor may prevent rotation of the breast implant. The outer surface of the shell may be non-textured.

Implementations of the breast implant may include one, all, or any of the following:

The breast implant may include an anatomical shape.

The anchor may form a lip at the interface between the anterior caudal portion and the anterior cephalic portion.

The anchor may include a recess configured to be filled by a fluid within the breast implant.

The anchor may be directly and fixedly coupled to the posterior cephalic portion.

An entirety of an inner surface of the anterior caudal portion and the posterior caudal portion may be directly and fixedly coupled to the anchor.

The anchor and the shell may be continuously formed from a same material.

Implementations of a breast implant may include a shell including a posterior cephalic portion, a posterior caudal portion, an anterior cephalic portion, and an anterior caudal portion. Implementations of the breast implant may also include an anchor coupled within the shell and coupled directly and fixedly to the posterior caudal portion and the anterior caudal portion. The anchor may provide a recess therein. Implementations of the breast implant may include a fluid included in the recess and the shell. The anchor may prevent rotation of the breast implant. The anchor may prevent flipping of the breast implant. The outer surface of the shell may be non-textured. The breast implant may include an anatomical shape. The fluid may be directly in contact with an entire inner surface of the anterior cephalic portion of the shell.

Implementations of the breast implant may include one, all, or any of the following:

The anchor may be configured to prevent buckling of the breast implant.

The anchor may form a lip at the interface between the anterior caudal portion and the anterior cephalic portion.

The anchor may extend around a perimeter of a posterior portion of the shell, wherein the posterior portion includes the posterior cephalic portion and the posterior caudal portion.

An entirety of an inner surface of the anterior caudal portion and the posterior caudal portion may be directly and fixedly coupled to the anchor.

The anchor may extend from a base of the posterior portion to a top of the posterior portion. The posterior portion may include the posterior cephalic portion and the posterior caudal portion.

The anchor and the shell may be continuously formed from the same material.

Implementations of a breast implant may include a shell including a posterior portion and an anterior portion. The breast implant may also include an anchor coupled within the shell and coupled directly and fixedly to an entire interface on an inner surface of the shell between the posterior portion and the anterior portion. The anchor may prevent flipping of the breast implant. An outer surface of the shell may be non-textured.

Implementations of the breast implant may include one, all, or any of the following:

The breast implant may be a round implant.

The anchor may form a cross directly and fixedly coupled to the anterior portion.

The anchor may be directly and fixedly coupled to an entire inner surface of the posterior portion.

The anchor may include a solid implant having a recess formed therein. The recess may be filled with a fluid medium.

The anchor and the shell may be continuously formed from a same material.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DESCRIPTION

This disclosure, its aspects and implementations, are not limited to the specific components, assembly procedures or method elements disclosed herein. Many additional components, assembly procedures and/or method elements known in the art consistent with the intended breast implants will become apparent for use with particular implementations from this disclosure. Accordingly, for example, although particular implementations are disclosed, such implementations and implementing components may comprise any shape, size, style, type, model, version, measurement, concentration, material, quantity, method element, step, and/or the like as is known in the art for such breast implants, and implementing components and methods, consistent with the intended operation and methods.

Figure 1:
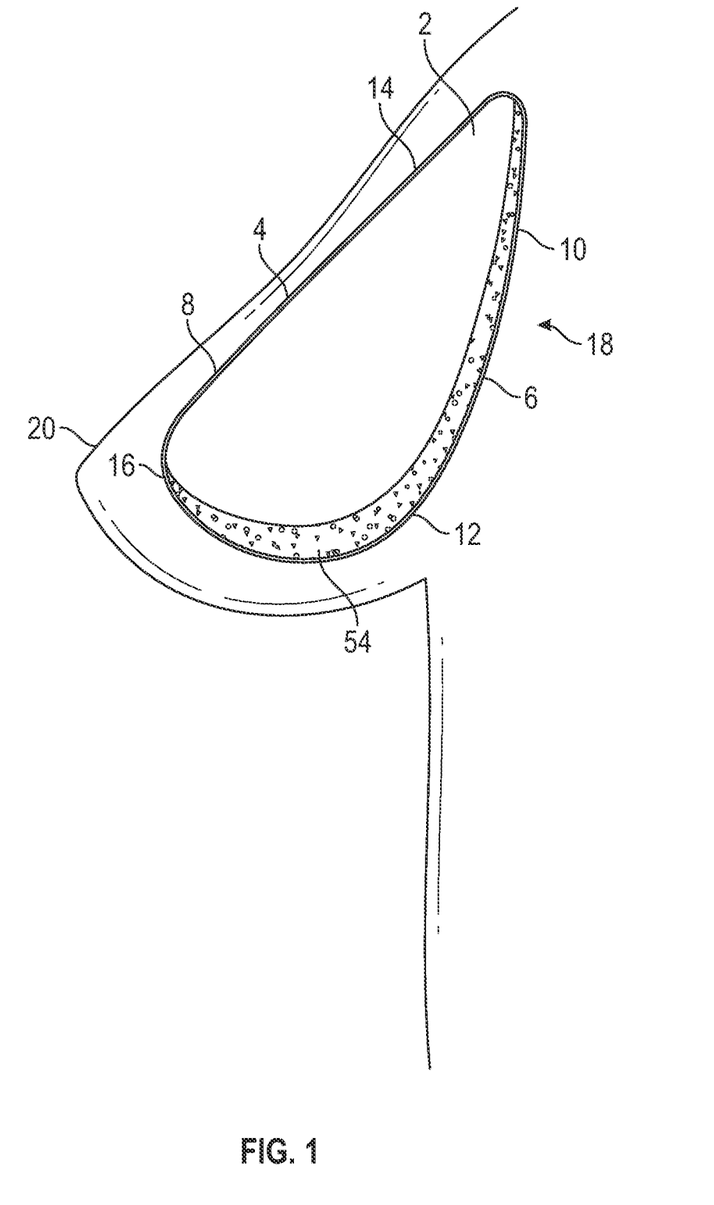
FIG. 1 is a cross sectional side view of a breast implant placed within a breast.

Referring to FIG. 1, a cross-sectional side view of an implementation of a breast implant placed within a breast is illustrated. The breast implant 2 includes a shell 4. The shell 4 of the breast implant includes a posterior portion 6. The posterior portion 6 forms the outer back wall of the breast implant configured to face the chest wall 18 of a user when the breast implant 2 is placed within a breast. In various implementations (and as illustrated by FIGS. 1-4), the outer back wall of the breast implant may be substantially flat. The shell also includes an anterior portion 8. The anterior portion 8 is configured to face away from the chest wall 18 and towards the front 20 of the breast when the breast implant is placed within a breast. The posterior portion 6 includes a posterior cephalic portion 10 and a posterior caudal portion 12. The anterior portion 8 includes an anterior cephalic portion 14 and an anterior caudal portion 16.

Figure 4:
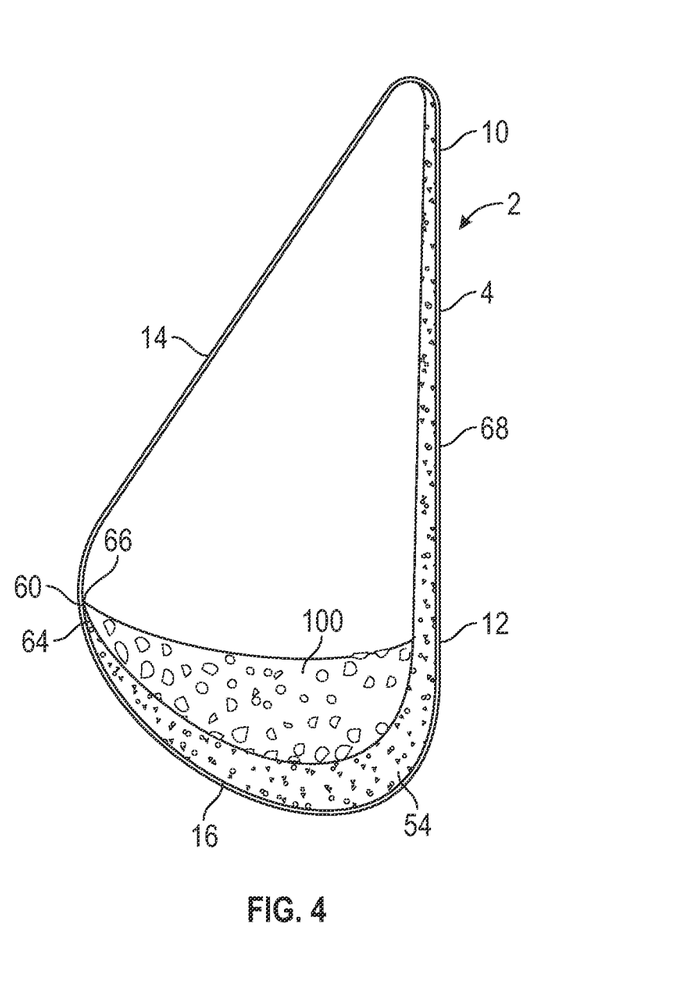
FIG. 4 is a cross sectional side view of the breast implant of FIG. 1.

Words used to describe positions or locations of portions of the breast implant used herein, such as, by non-limiting example, top, bottom, front, back, up, down, vertical, and horizontal are understood to indicate the position, orientation, or location of the breast implant when it is in a position where the back sidewall of the breast implant is vertical (as illustrated by FIG. 4 and similar to the position of the breast implant when properly placed within a breast of a recipient who is in a standing position, such as is illustrated by FIG. 1). The front and back of the implant are understood as respectively corresponding with the surface of the breast implant that faces towards the front of the user when inserted within a breast and the surface of the breast implant that faces towards the back of the user when inserted within a breast. Accordingly, if the breast implant is rotated this does not change what may be referred to as, for example, the back of the breast implant.

Figure 2:
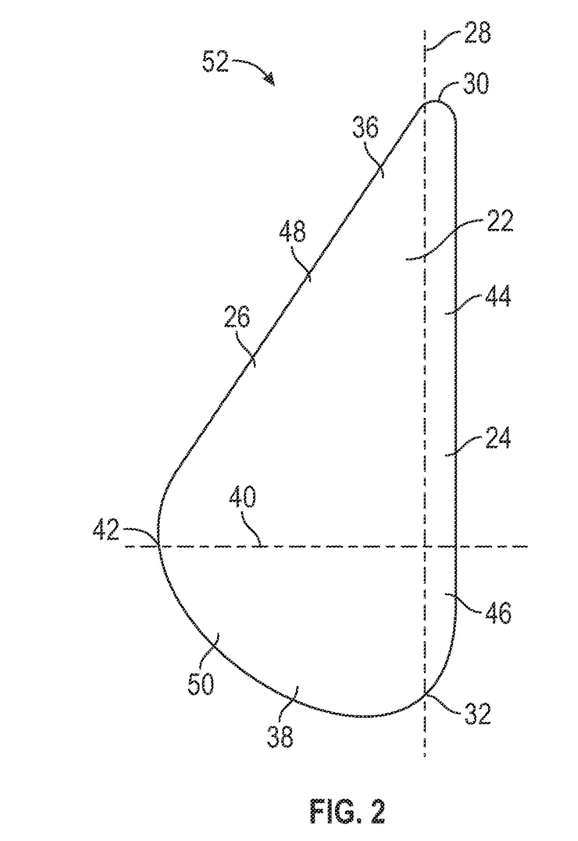
FIG. 2 is a side view of a breast implant illustrating the different sections of the shell.
Figure 3:
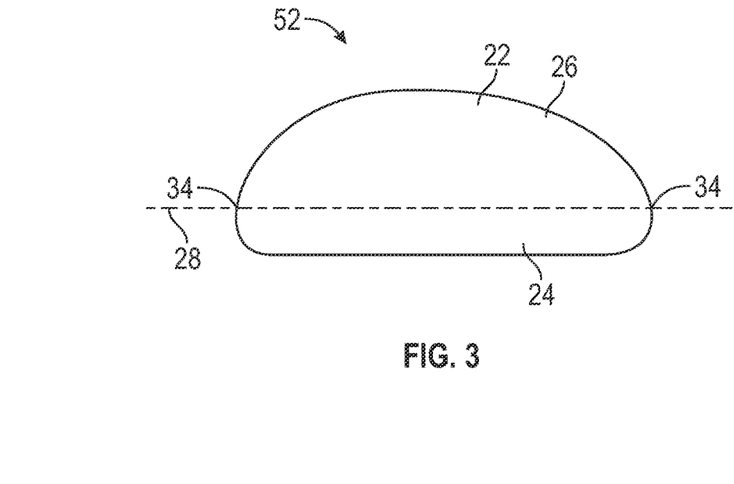
FIG. 3 is a top view of the breast implant of FIG. 2.

Referring to FIG. 2, a side view of a breast implant illustrating the four different portions of the shell (and in turn, the four different portions of the breast implant) is illustrated. FIG. 2 delineates where the different portions of the shell 22 begin and end. As illustrated, the interface between the posterior portion 24 of the shell 22 of the breast implant 52 and the anterior portion 26 of the shell is formed by plane 28. While plane 28 is illustrated as a single line in FIG. 2, it is understood that the plane extends into and out of the page. Referring to FIG. 3, a top view of the breast implant of FIG. 2 is illustrated. In this view plane 28 is also illustrated as a single line. It is understood that the plane 28 of FIG. 3 is illustrated as a single line inasmuch as plane 28 extends into and out of the page. As illustrated by FIG. 2, when the breast implant 52 is oriented with the back sidewall of the implant in a substantially vertical position, plane 28 extends from an apex 30 of the breast implant 52 to a lowest point 32 of the breast implant where the back of the breast implant no longer slopes downwards. Similarly, as illustrated by FIG. 3, when viewed from above the plane 28 extends through the outer most points 34 on the two opposing sides of the breast implant 52. As illustrated, the outer most points 34 are also inflection points inasmuch as the curvature of the slope of the sides of the breast implant 52 change at these points.

Referring back to FIG. 2, the interface between the cephalic portion 36 of the shell 22 the caudal portion 38 of the shell is formed along plane 40. While plane 40 is illustrated as a single line in FIG. 2, it is understood that the plane extends into and out of the page, rendering the plane 40 as a single line. When the breast implant 52 is oriented in a vertical position, as illustrated by FIG. 2, plane 40 extends from the furthest frontward point 42 of the breast implant 52 and is perpendicular to plane 28. The furthest frontward point 42 is also an inflection point where the curvature of the breast implant changes from sloping to the apex 30 to sloping to the lowest point 32.

Planes 28 and 40 intersect perpendicularly and form four different portions of the shell 22, the posterior cephalic portion 44, the posterior caudal portion 46, the anterior cephalic portion 48, and the anterior caudal portion 50. The posterior cephalic portion and the posterior caudal portion are part of the posterior portion 24. The anterior cephalic portion 48 and the anterior caudal portion 50 are part of the anterior portion 26. In addition to planes 28 and 40 dividing the shell into four different portion, planes 28 and 40 also divide the breast implant 52 into a posterior cephalic portion, a posterior caudal portion, an anterior cephalic portion, and an anterior caudal portion, each of these portions corresponding to the associated respective portions of the shell 22. The posterior cephalic portion, the posterior caudal portion, the anterior cephalic portion, and the anterior caudal portion of the various implementations of the breast implants and shells disclosed herein are understood to correspond to these respective portions as defined in relation to FIGS. 2-3.

Figure 5:
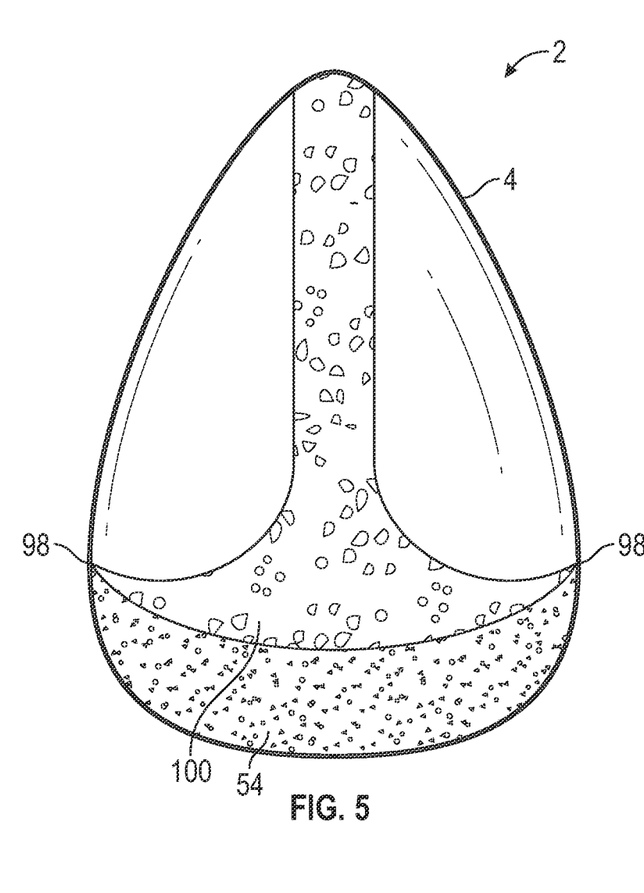
FIG. 5 is a perspective view of the breast implant of FIG. 1 with the shell illustrated as transparent.
Figure 6:
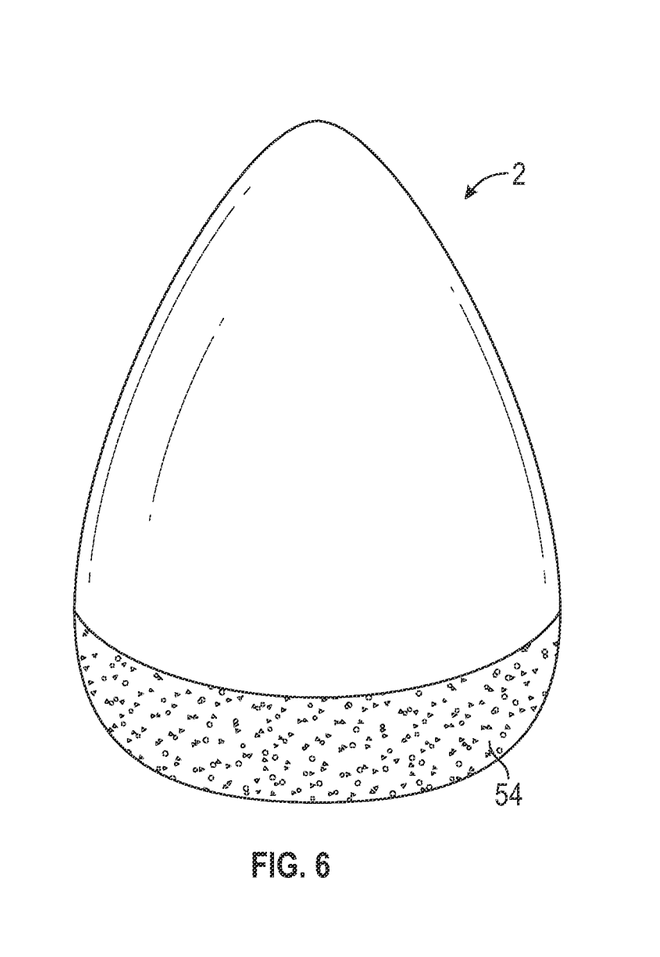
FIG. 6 is a front view of the breast implant of FIG. 1.
Figure 7:
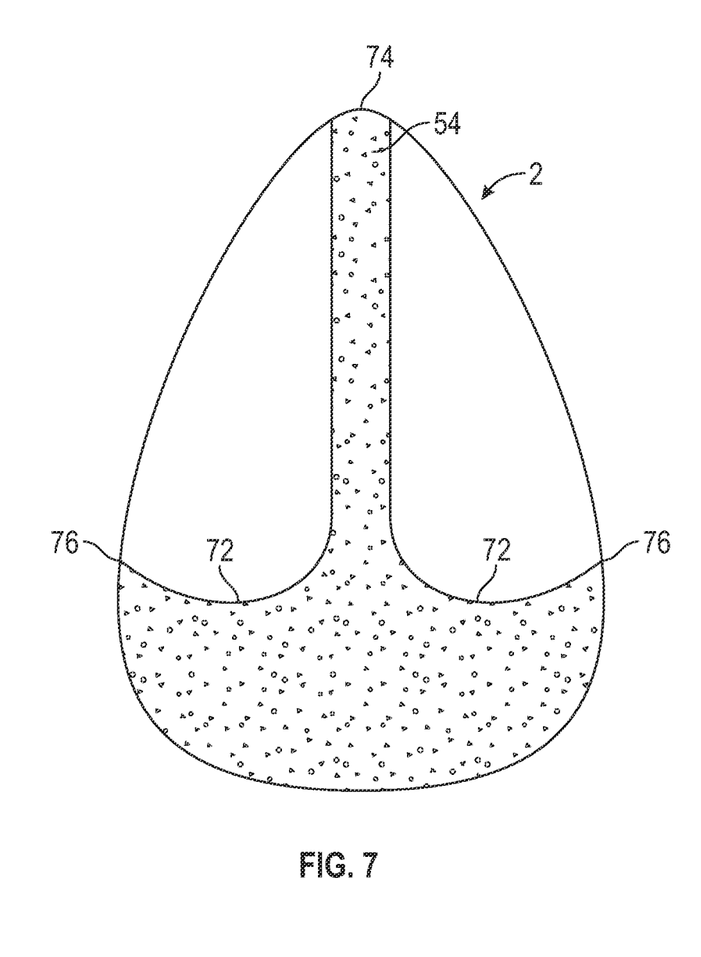
FIG. 7 is a rear view of the breast implant of FIG. 1.

Referring to FIGS. 4-7, various views of the implementation of the breast implant of FIG. 1 are illustrated. Referring specifically to FIG. 4, a cross sectional side view of the breast implant of FIG. 1 is illustrated. Referring to FIG. 5, a perspective view of the breast implant of FIG. 1 with the shell illustrated as transparent is illustrated. Referring to FIG. 6, a front view of the breast implant of FIG. 1 is illustrated. Referring to FIG. 7, a rear view of the breast implant of FIG. 1 is illustrated.

In various implementations, and as illustrated by FIGS. 1-7, the breast implant may include an anatomical shape. As used herein, "anatomical shape" is understood to mean a shape corresponding to a natural breast, a teardrop shape, a pear shape, and/or the shape of an ovoid. In such implementations, the anatomical breast implant may provide a more natural look when inserted into a breast. In particular implementations, the breast implant may be configured to have the majority of its volume rest below the nipple of the breast when inserted into the breast. In such implementations, the breast implant may be configured to have 55-60% of the volume of the implant below the nipple of the breast when the breast implant is inserted into the breast. In other implementations the breast implant may include a round shape (as illustrated by FIGS. 12-18).

Referring back to FIGS. 1 and 4-7, the breast implant 2 includes a shell 4 that may be made from silicone or any other material used in constructing breast implants. In various implementations, the shell, and in turn the breast implant, may have a smooth and non-textured exterior surface. In other implementations, any of the breast implants disclosed herein may include a shell having a textured outer surface.

Still referring to FIGS. 1 and 4-7, in various implementations the breast implant 2 includes an anchor 54 directly and fixedly coupled to an interior surface of the shell 4. As used herein, "fixedly coupled" is defined as the anchor being attached to the shell in a non-moveable manner with relation to the portion of the shell that the anchor is directly coupled to. FIG. 1 illustrates a cross sectional view of the anchor. FIG. 4 illustrates both a cross sectional view of the anchor as well as the inner view of a portion of the anchor directly coupled to the shell. FIG. 5 illustrates the outer surface of the portion of the anchor fixed to the front of the shell and the inner surface of the portion of the anchor fixed to the back of the shell. The shell of FIG. 5 is illustrated as transparent in order to illustrate the position of the anchor. FIG. 6 illustrates a front view of the anchor and FIG. 7 illustrates a back view of the anchor. The portion of the shell covering the respective portions of the anchor of FIGS. 6 and 7 is illustrated as transparent in order to show the relative position of the anchor. It is understood that the anchor of the breast implant of FIGS. 1 and 4-7 may not be visible from an external view inasmuch as the anchor would be covered by the shell.

In various implementations the anchor 54 may be a semi-solid or a solid material. In particular implementations the anchor 54 may include a material used in other solid implants, such as a calf implant. In various implementations the type of material of the anchor 54 may be different from the type of material of the shell 4. In other implementations, the type of material of the anchor 54 may be the same as the type of material of the shell 4. In various implementations the anchor 54 and the shell 4 are two distinct elements fixedly coupled together in such a way that a boundary is visible between the anchor and the shell in a cross-sectional side view of the breast implant. In other implementations the anchor and the shell may be made from one continuous piece of material. In such implementations where the anchor and the shell are made from a single continuous piece of material, there would not be a visible boundary between the anchor and the shell in a cross-sectional side view of the breast implant. With this said, in such implementations the breast implant is still considered as having both a shell and an anchor fixed to the shell, with the shell being the outer most portion of the implant and the anchor being the solid implant portion of the breast implant fixed to the shell and configured to prevent unwanted rotation of the breast implant.

Referring Specifically to FIG. 4, the anchor 54 is directly and fixedly coupled to the bottom of the breast implant 2. In various implementations, the anchor 54 is directly and fixedly coupled to the posterior caudal portion 12 of the shell 4. In particular implementations, the anchor may be directly and fixedly coupled to both the posterior caudal portion 12 of the shell 4 and the anterior caudal portion 16 of the shell 4. In various implementations the anchor 54 may be directly and fixedly coupled to only a portion of the inner surface of the posterior caudal portion 12 of the shell 4, only a portion of the inner surface of the anterior caudal portion 16 of the shell 4, an entirety of the inner surface of the posterior caudal portion 12 of the shell 4 (as illustrated by FIG. 7), an entirety of the inner surface of the anterior caudal portion 16 of the shell 4 (as illustrated by FIG. 6), or any combination thereof.

In various implementations, and as illustrated by FIG. 4, the anchor may extend to a furthest most forward point 60 of the breast implant 2. In such implementations, the furthest most forward point 60 may lie on the interface 66 between the anterior caudal portion 16 and the anterior cephalic portion 14 of the shell 4. In such implementations, the anchor 54 may form a lip 64 at the interface between the anterior caudal portion and the anterior cephalic portion. The lip is formed due to the solid properties of the anchor in contrast to the flexible properties of the shell of the anterior cephalic portion 14.

Referring to FIGS. 4-5 and 7, in various implementations the anchor 54 may extend up a portion of the back sidewall of the shell 4. In various implementations the anchor 54 does not extend above a midpoint 68 of the back sidewall. In other implementations, the anchor 54 may extend above the back sidewall. In various implementations, the anchor may be fixedly and directly coupled to the posterior cephalic portion 10 of the shell 4. In other implementations the anchor may not be directly coupled to the posterior cephalic portion 10 of the shell 4.

In various implementations, and as illustrated by FIGS. 4-5 and 7, the anchor 54 may extend to a top of the inner surface of the shell of the breast implant. In such implementations, the anchor 54 may extend from a base of the posterior portion to a top of the posterior portion of the shell 4. In particular implementations, and as illustrated by FIGS. 4-5 and 7, the portion of the anchor that extends to the top of the inner surface of the shell of the breast implant may include a narrow strip.

In various implementations, and as illustrated by FIG. 7, the portion of the anchor directly coupled to the back sidewall of the shell may form a shape having an upper perimeter having three peaks and two valleys 72 (similar to the shape of a W). In various implementations, the central peak 74 may extend further upwards than the outer two peaks 76. In other implementations, all three peaks may extend upwards to a same height, and in still other implementations, the central peak may not extend upwards as much as the outer two peaks.

Figure 8:
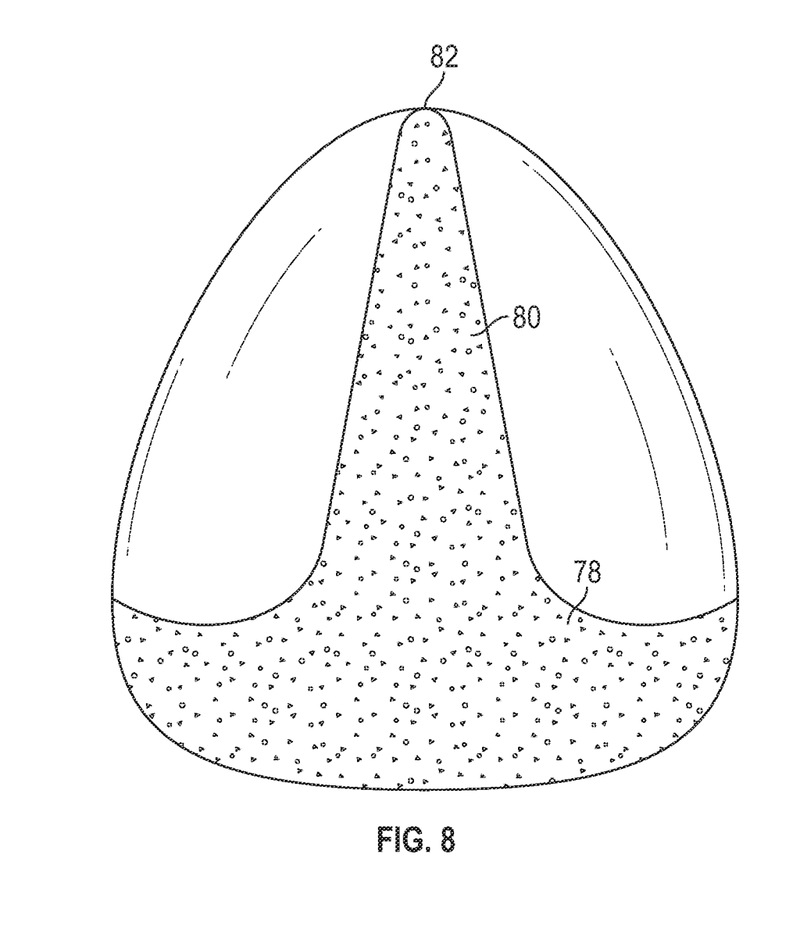
FIG. 8 is a rear view of a second implementation of a breast implant.
Figure 9:
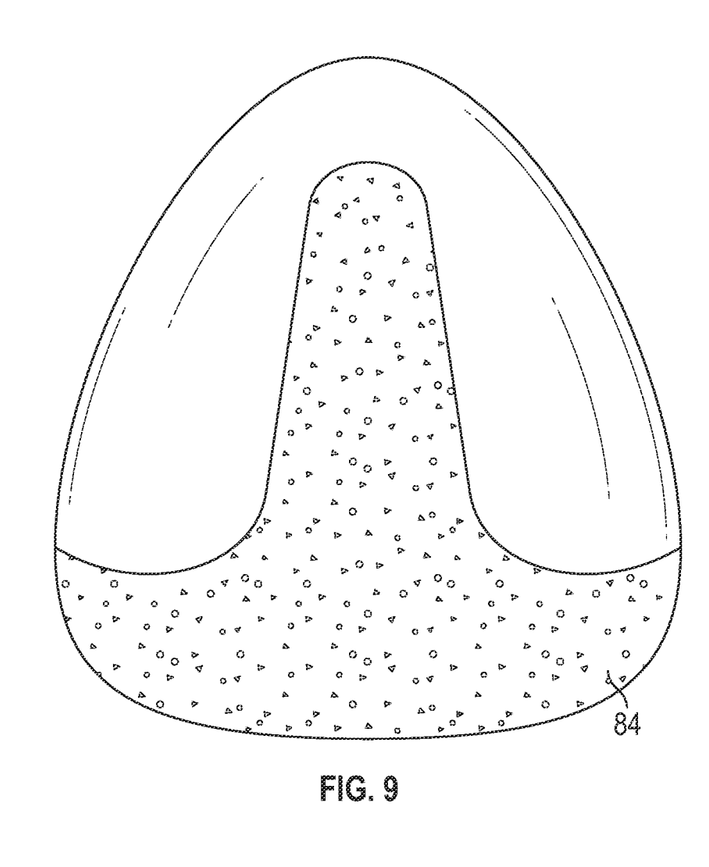
FIG. 9 is a rear view of a third implementation of a breast implant.
Figure 10:
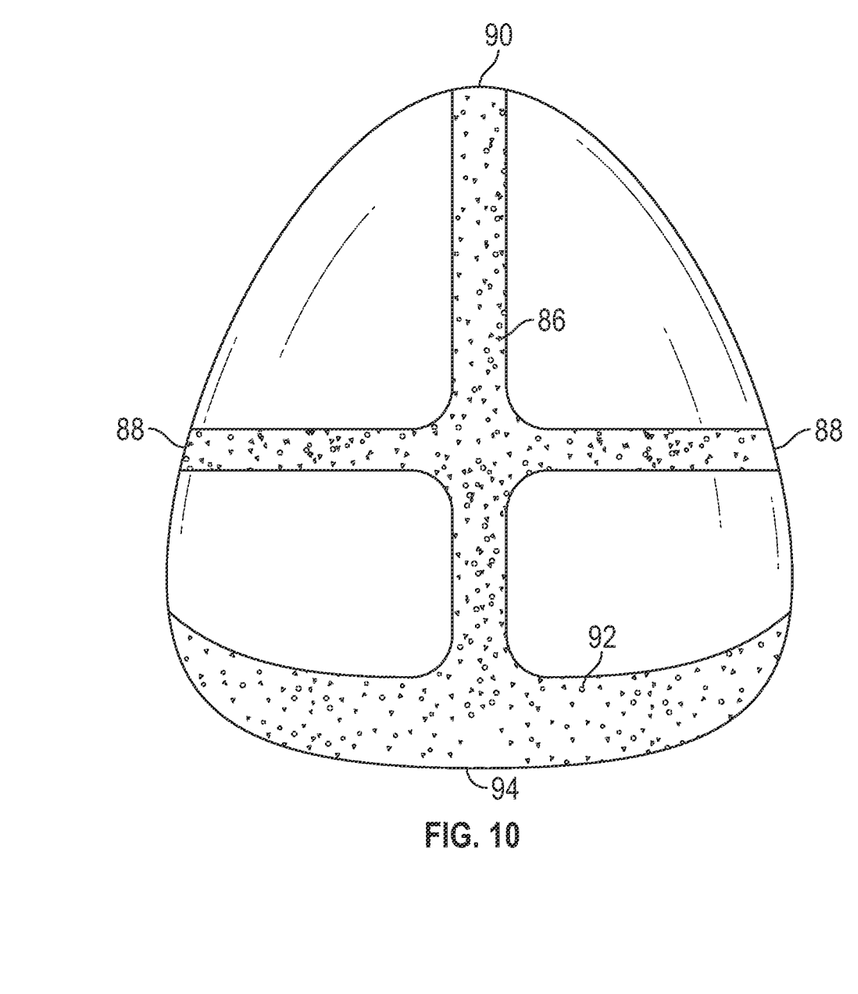
FIG. 10 is a rear view of a fourth implementation of a breast implant.
Figure 11:
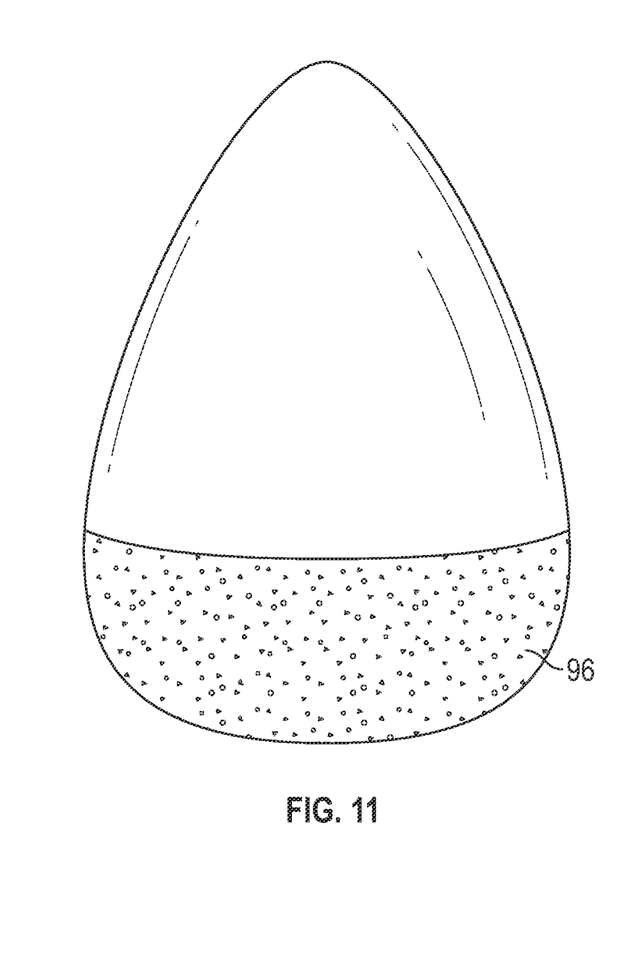
FIG. 11 is a rear view of a fifth implementation of a breast implant.

In other implementations, the portion of the anchor directly coupled to the posterior portion of the shell may form a shape differing from the shape illustrated in FIG. 7. Referring to FIG. 8, a rear view of a second implementation of a breast implant is illustrated. In various implementations the portion of the anchor 78 directly coupled to the posterior portion of the shell may be similar to the shape illustrated by FIG. 7 with the difference being that the portion 80 of the anchor that extends to the top 82 of the posterior portion may taper and gradually reduce in width as the portion extends upwards. Referring to FIG. 9, a rear view of a third implementation of a breast implant is illustrated. In various implementations the portion of the anchor 84 directly coupled to the posterior portion of the shell may be similar to the shape illustrated by FIG. 8 with the difference being that the portion 84 does not extend all the way to the top of the posterior portion of the shell. Referring to FIG. 10, a rear view of a fourth implementation of a breast implant is illustrated. In various implementations the portion of the anchor 86 directly coupled to the posterior portion of the shell may form a cross with a first portion of the cross extending from two opposing sides 88 of the posterior portion and a second portion of the cross extending from a top 90 of the posterior portion to the remainder 92 of the anchor (or non-cross portion of the anchor) at the bottom 94 of the posterior portion. In other implementations, the cross portion, or the portion of the anchor directly coupled to the posterior portion of the shell, may not extend all the way to the opposing sides 88, all the way to the top 90 of the posterior portion, and/or all the way to the remainder 92 of the anchor at the bottom 94 of the posterior portion. Referring to FIG. 11, a rear view of a fifth implementation of a breast implant is illustrated. In various implementations the upper edge of the portion of the anchor 96 directly coupled to the posterior portion of the shell may form a substantially straight line across the posterior portion of the shell. In particular implementations the upper edge may coincide with the interface between the posterior caudal portion and the posterior cephalic portion. As used herein, "interface" refers to the junction between two separate portions. In other implementations, rather than a substantially straight line the upper edge may form a line having a concave or convex curve that extends between two opposing sides of the posterior portion of the shell. In still other implementations, the portion of the anchor directly coupled to the posterior portion may form any other shape, design, and/or pattern different from the implementations illustrated by FIGS. 7-11.

In various implementations the anchor is not directly coupled to the anterior cephalic portion of the shell. In such implementations, the fluid medium used to fill the breast implant may be in direct contact with an entire inner surface of the anterior cephalic portion of the shell. In other implementations, the anchor may be directly coupled to portions of the anterior cephalic portion of the shell. In such implementations, the thickness of the anchor directly coupled to the anterior cephalic portion of the shell is less than the thickness of the anchor directly coupled to the posterior caudal portion of the shell.

In various implementations, the thickness of the anchor may remain constant across the entire area of the anchor. In other implementations, and as illustrated by FIG. 4, the thickness of the anchor of any implementation of a breast implant disclosed herein may vary. In various implementations, the thickest portion of the anchor may be directly coupled to the posterior caudal portion of the shell. In particular implementations, the lowest portion of the shell of the breast implant may be directly coupled to the thickest portion of the anchor. In various implementations, the anchor may reduce in thickness as it extends away from the thickest portion of the anchor directly coupled to the lowest portion of the shell. More specifically, in various implementations the thickness of the anchor may reduce as the anchor extends towards the top of the breast implant 2 along the posterior portion of the shell. Similarly, the thickness of the anchor may reduce in thickness as the anchor extends towards the front of the breast implant 2 along the anterior caudal portion of the shell. Similarly, the thickness of the anchor may reduce as the anchor extends towards the outer side edges 98 of the anchor, as illustrated by FIG. 5.

In various implementations, the thickness of any anchor disclosed herein may include any thickness or any number of thicknesses, ranging between 2-10 mm. In other implementations, the thickness of the anchor of the breast implant may include a thickness less than 2 mm or more than 10 mm. In particular implementations, the thickness of the anchor may range between 2-4 mm. In various implementations, the exact dimensions and/or the thickness of the anchor may be optimized and customized based upon the anatomy and needs of the recipient of the breast implant.

In various implementations, and as illustrated by FIGS. 4-5, the anchor 54 may include a recess 100 formed therein. In such implementations, the breast implant may be considered a hybrid breast implant (both solid implant and fluid filled implant) inasmuch as the breast implant includes a solid implant having a lumen inasmuch as the anchor is made from a solid or semi-solid material and has a lumen, or recess 100, formed therein.

The shell 4 of the breast implant 2 is filled with a fluid medium. "Fluid medium" and "fluid," as used herein, may include a silicone-gel, saline, or any other fluid or semi-fluid material used to fill a breast implant. In implementations where the anchor includes a recess, the fluid medium fills the recess of the anchor.

The implementations of the breast implants disclosed herein having an anchor result in a breast implant with varying weight distribution. In such implementations, the breast implant may be heavier towards the anterior caudal and/or posterior caudal portions of the breast implant due to the anchor being directly coupled to these portions of the shell. In turn, the breast implant may naturally settle in these areas which may correspond to the lower portion of the breast curve of a breast and/or towards the chest wall of the user. In turn, the anchor may prevent unwanted rotation of the breast implant within a breast due to the heavier portions of the breast implant naturally settling in the corresponding lower portions of the breast. This varied weight distribution prevents the lighter upper end of the implant from rotating to the bottom of the breast. The varied weight distribution prevents rotation of the breast implant along an axis of rotation substantially perpendicular to the chest wall of the user (or rotation where the posterior portion of the implant still faces the chest wall of the user but the upper portion of the breast implant rotates down to the bottom of the breast) as well as rotation of the breast implant along an axis of rotation substantially parallel to the chest wall of the user. "Flipping," as used herein, may refer to rotation of the breast implant along an axis of rotation substantially parallel to the chest wall (where the posterior portion of the breast implant is flipped to face the front of the breast and the anterior portion of the implant faces the chest wall of the user). In addition to the varied weight distribution preventing unwanted flipping or rotation, in implementations of breast implants disclosed herein having the anchor directly and fixedly coupled to the posterior portion of the shell, the anchor may prevent flipping of the implant inasmuch as the anchor provides a level of rigidity to the posterior portion of the breast implant. In turn, the breast implant will not be able to flip due to the stiffness of the anchor interfering with the chest wall of the user. The anchor prevents the breast implant from rolling over on itself or folding which prevents flipping of the implant. This is contrary to implementations not having an anchor where the implant may be capable of rolling over on itself and flipping.

Implementations of the breast implant disclosed herein may prevent unwanted rotation of the breast implant within a breast while still being able to have a smooth or non-textured outer surface of the shell of the breast implant. Because of this, implementations of the breast implant disclosed herein may insure a proper position and orientation of the breast implant while also decreasing the risk of cancer (such as Anaplastic Large Cell Lymphoma) caused by textured surfaces interfering with the capsule surrounding the breast implant.

The implementations of breast implants including an anchor disclosed herein may also reduce the feeling of rippling and/or buckling experienced by many breast implant recipients. In various implementations, the lowest portion of a breast may become the most thinned out or stretched portion of the breast due to the lowest portion of the breast carrying the majority of the weight of the breast implant. Due to this, the lowest portion of the breast may be most susceptible to the ability to feel flaws or edges of the breast implant, including any rippling or buckling of the breast implant. In implementations having the anchor, the increased support from the anchor at the bottom portion of the breast implant corresponding to the lowest portion of the breast may add structural integrity to the bottom portion of the breast implant, thereby minimizing and/or eliminating any rippling and/or buckling of the breast implant.

Figure 12:
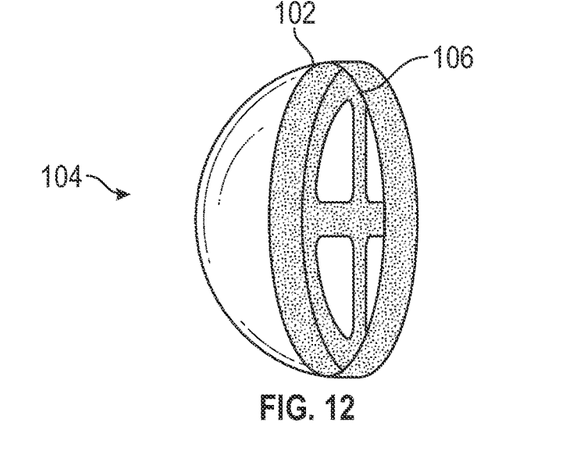
FIG. 12 is a front perspective view of a round breast implant.
Figure 13:
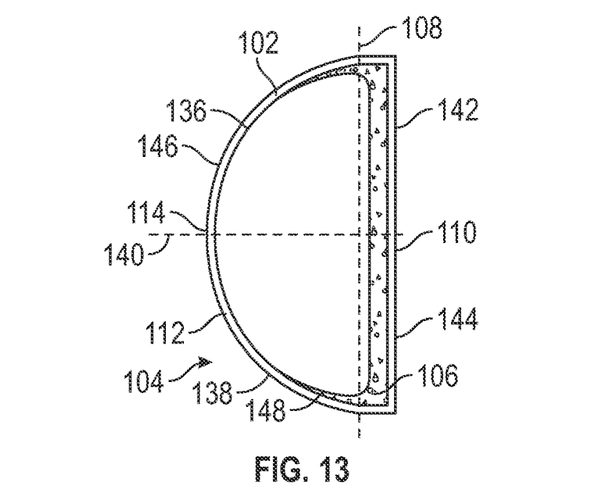
FIG. 13 is a cross-sectional side view of the round breast implant of FIG. 12.
Figure 14:
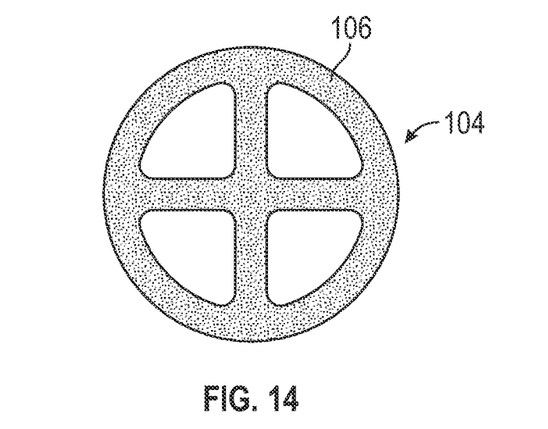
FIG. 14 is a rear view of the implant of FIG. 12.

While various implementations disclosed herein discuss breast implants having an anatomical shape, implementations of round implants may also include a shell similar to the shell of the anatomical implant with the difference being that the round implant includes a round shape as illustrated by FIGS. 12-18, rather than an anatomical or tear-drop shape. Implementations of round implants may also include a fluid medium and an anchor, either of which may be respectively the same as or similar to any fluid medium or anchor disclosed herein. In particular implementations, the anchor within a round implant may include the same material and/or relative thicknesses as any anchor disclosed herein, but may include a shape unique to a round implant. Referring to FIG. 12, a perspective view of a round breast implant is illustrated. FIG. 12 is illustrated with the shell 102 of the breast implant 104 illustrated as transparent in order to show the position of the anchor 106 coupled to the inner surface of the shell. Referring to FIG. 13, a cross sectional side view of the breast implant of FIG. 12 is illustrated. Referring to FIG. 14, a rear view of the implant of FIG. 12 is illustrated. FIG. 14 illustrates the shell as transparent in order to show the shape of the portion of the anchor directly coupled to posterior portion of the shell 102 of the breast implant 104.

Referring to FIG. 13, the shell 102 includes a posterior portion 110 and an anterior portion 112 divided by an interface formed along plane 108. While plane 108 is illustrated as a single line, plane 108 extends into and out of the page of FIG. 13. With respect to the round implant, the interface between the posterior portion and the anterior portion may be defined by where the shell of the implant begins to slopes towards the most forward point 114 of the breast implant. The shell 102 also includes a cephalic portion 136 and a caudal portion 138 separated by an interface formed along plane 140. While plane 140 is illustrated as a single line, plane 140 extends into and out of the page of FIG. 13. In turn, the shell 102 includes a posterior cephalic portion 142, a posterior caudal portion 144, an anterior cephalic portion 146, and an anterior caudal portion 148. The plane 140 may extend through the most forward point 114 of the breast implant (or the frontward most apex of the implant) and may be perpendicular to plane 108.

In various implementations the type of material of the anchor 106 may be different from the type of material of the shell 102. In other implementations, the type of material of the anchor 106 may be the same as the type of material of the shell 102. In various implementations the anchor 106 and the shell 102 are two distinct elements fixedly coupled together in such a way that a boundary is visible between the anchor and the shell in a cross-sectional side view of the breast implant. In other implementations the anchor and the shell may be made from one continuous piece of material. In such implementations where the anchor and the shell are made from a single continuous piece of material, there would not be a visible boundary between the anchor and the shell in a cross-sectional side view of the breast implant. With this said, in such implementations the breast implant is still considered as having both a shell and an anchor fixed to the shell, with the shell being the outer most portion of the implant and the anchor being the solid implant portion of the breast implant fixed to the shell and configured to prevent unwanted flipping of the breast implant.

In various implementations, the anchor 106 may be directly and fixedly coupled to the posterior portion of the shell of the breast implant. In particular implementations the anchor may extend to an upper most portion of the shell and a lower most portion of the shell. In such implementations, the anchor may prevent unwanted flipping inasmuch as the anchor provides rigidity to the posterior portion of the shell and will prevent the posterior portion of the shell from folding or rolling over on itself. In turn, if the breast implant were to start to flip the chest wall of the user would interfere with the anchor attempting to flip and would prevent the breast implant from flipping.

In particular implementations the anchor is not directly coupled to the anterior portion of the shell 102. In other implementations, the anchor 106 may be directly coupled to a portion of the anterior portion of the shell directly adjacent to the interface between the posterior portion and the anterior portion. In various implementations, the majority of the inner surface of the anterior portion of the shell is still in direct contact with a fluid medium within the implant. In other implementations, the anchor may extend further towards the most forward point 114 or not as close to the most forward point than what is illustrated by FIGS. 12 and 13. The particular location of the anchor directly and fixedly coupled to the anterior portion of the shell may be varied based upon the anatomy and needs of a particular individual receiving the breast implant.

In various implementations the breast implant may be symmetrical. In such implementations, the portion of the anchor directly coupled to the cephalic portion of the shell may be the same as the portion of the anchor directly coupled to the caudal portion of the shell. In such implementations, the round implant may be configured to rotate along an axis perpendicular to the chest wall of the recipient without having the breast implant appear or feel as though it were upside down inasmuch as the portions of the anchor closest to the top of the breast and the bottom of the breast will be the same regardless of how the breast implant may be rotating along an axis perpendicular to the chest wall of the recipient.

In implementations where the anchor is coupled to the anterior portion and the posterior portion, the anchor may include a recess formed therein. In such implementations, the recess may be filled with a fluid medium. In such implementations, the breast implant may be considered a hybrid breast implant (both solid implant and fluid filled implant) inasmuch as the breast implant includes a solid implant having a lumen inasmuch as the anchor is made from a solid or semi-solid material and has a lumen, or recess, formed therein.

Still referring to FIG. 13, an implementation of a thickness of the anchor is illustrated. In various implementations, the thickness of the anchor may taper towards the edges of the anchor. In other implementations the thickness of the anchor may vary from what is illustrated by FIG. 13.

In particular implementations the anchor may be directly coupled to an entire interface on the inner surface of the shell between the posterior portion and the anterior portion. In such implementations, the anchor forms a perimeter around the shell (and also around the posterior portion of the shell). While this is illustrated in conjunction with the round implant of FIGS. 12-14, it is understood that the anatomically shaped implants disclosed herein may also include an anchor that extends around the perimeter of the posterior portion of the shell. In implementations of a round implant including an anchor formed around the perimeter of the shell, even if the implant rotates about an axis perpendicular to the chest wall of the user, the anchor always extends from the portion of the implant closest to the top of the breast to the portion of the implant closest to the bottom of the breast. In turn, the anchor prevents unwanted flipping of the implant inasmuch as the rigidity of the anchor prevents the implant from folding or rolling over on itself even if the round breast implant rotates along an axis perpendicular to the chest wall of the user.

Figure 15:
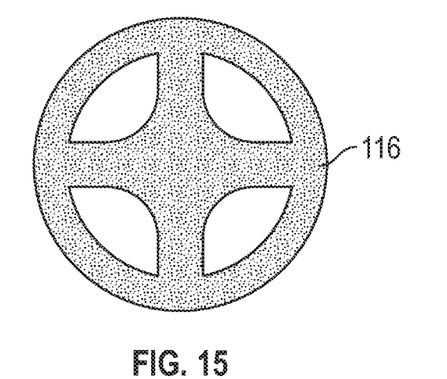
FIG. 15 is a rear view of a second implementation of a round implant.
Figure 16:
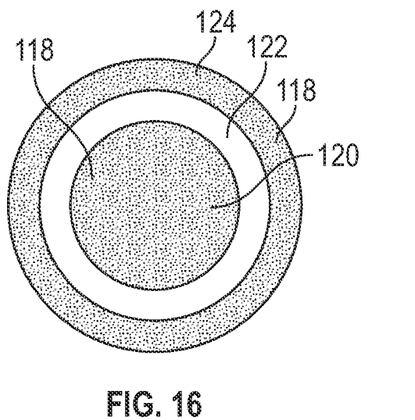
FIG. 16 is a rear view of a third implementation of a round implant.
Figure 17:
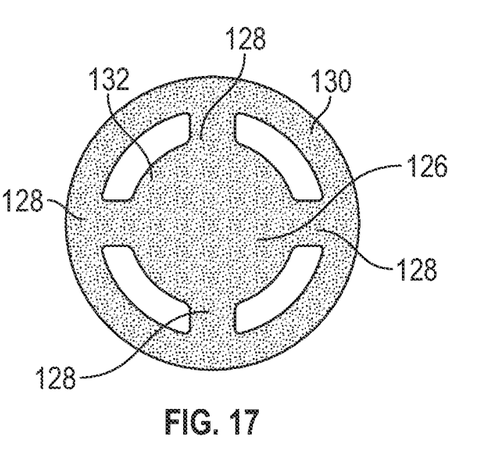
FIG. 17 is a rear view of a fourth implementation of a round implant.
Figure 18:
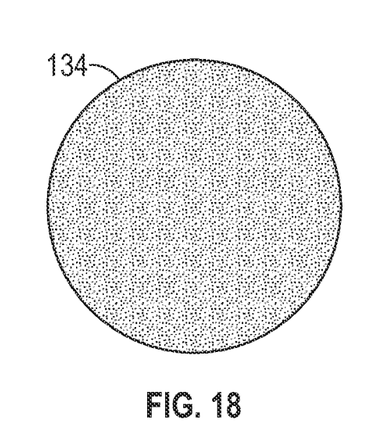
FIG. 18 is a rear view of a fifth implementation of a round implant.

In various implementations, and as illustrated by FIGS. 12 and 14, the anchor 106 may form a cross directly coupled to the posterior portion of the shell. In other implementations, the portion of the anchor directly coupled to the posterior portion of the shell may form a different shape. Referring to FIG. 15, a rear view of a second implementation of a round implant is illustrated. In various implementations, the portion of the anchor 116 directly coupled to the posterior portion may be similar to the anchor of FIG. 14, with the difference being that the corners formed by the cross may be more rounded. Referring to FIG. 16, a rear view of a third implementation of a round implant is illustrated. In various implementations the portion of the anchor 118 directly coupled to the posterior portion may include an outer ring 124 and an inner portion 120 separated from the outer ring by a gap 122. Referring to FIG. 17, a rear view of a fourth implementation of a round implant is illustrated. In various implementations, the portion of the anchor 126 directly coupled to the posterior portion of the shell may include an anchor similar to the anchor of FIG. 16, with the difference being that the anchor includes four separate bridges 128 connecting the outer ring 130 to the inner portion 132. Referring to FIG. 18, a rear view of a fifth implementation of a round implant is illustrated. In various implementations, the implant may include an anchor 134 directly and fixedly coupled to the entirety of the inner surface of the posterior portion of the shell. Any of the implants illustrated by FIGS. 15-18 may include an anchor that extends towards the anterior portion of the shell as illustrated by FIG. 13. In other implementations, anchors having other shapes that the shapes disclosed herein may be directly coupled to the shell of a round breast implant. The shells of FIGS. 15-18 are all illustrated as transparent in order to illustrate the respective anchors.

In various implementations, the anchors disclosed herein with round implants may prevent flipping of the implant by having the anchor directly and fixedly coupled to the posterior portion of the shell. In such implementations, the anchor may prevent flipping of the implant inasmuch as the anchor provides a level of rigidity to the posterior portion of the breast implant. In turn, the breast implant will not be able to flip due to the stiffness of the anchor preventing the anchor from folding or rolling over on itself. In turn, if the implant tries to flip, the anchor, which extends along the posterior portion, is blocked from flipping by the chest wall of the user. This is contrary to implementations not having an anchor where the implant may be capable of rolling over on itself and flipping.

Implementations of the round breast implants disclosed herein may prevent unwanted flipping of the breast implant within a breast while still being able to have a smooth or non-textured outer surface of the shell of the breast implant. Because of this, implementations of the breast implant disclosed herein may insure a proper position and orientation of the breast implant while also decreasing the risk of cancer (such as Anaplastic Large Cell Lymphoma) caused by textured surfaces interfering with the capsule surrounding the breast implant.

Implementations of the round implants disclosed herein may prevent rippling and/or buckling of the breast implant at portions of the breast implant directly coupled to the anchor. In various implementations where the anchor is directly coupled to the anterior portion of the shell, the anchor may also provide a desired shape and curve to a breast inasmuch as the anchor is capable of maintaining a shape or curve better than just the shell filled by the fluid medium.

In various implementations, a method of forming any of the breast implants disclosed herein may include scanning an intended recipient of the breast implants in order to determine the proper shape and size of the anchor to be formed within the breast implant. The breast implant may then be formed with customized dimensions in order to give the breast the most natural look and feel while also eliminating unwanted rotation, flipping, rippling, and/or buckling of the breast implant.

In places where the description above refers to particular implementations of breast implants and implementing components, sub-components, methods and sub-methods, it should be readily apparent that a number of modifications may be made without departing from the spirit thereof and that these implementations, implementing components, sub-components, methods and sub-methods may be applied to other breast implants.

What is claimed is:

1. A breast implant comprising:
   a shell comprising a posterior cephalic portion, a posterior caudal portion, an anterior cephalic portion, and an anterior caudal portion; and
   an anchor coupled within the shell and coupled directly and fixedly to the posterior caudal portion and the anterior caudal portion;
   wherein the anchor prevents rotation of the breast implant;
   wherein the anchor and the shell are continuously formed from a same material; and
   wherein an outer surface of the shell is non-textured.

2. The breast implant of claim 1, wherein the breast implant comprises an anatomical shape.

3. The breast implant of claim 1, wherein the anchor forms a lip at an interface between the anterior caudal portion and the anterior cephalic portion.

4. The breast implant of claim 1, wherein the anchor comprises a recess configured to be filled by a fluid within the breast implant.

5. The breast implant of claim 1, wherein the anchor is directly and fixedly coupled to the posterior cephalic portion.

6. The breast implant of claim 1, wherein an entirety of an inner surface of the anterior caudal portion and the posterior caudal portion is directly and fixedly coupled to the anchor.

7. A breast implant comprising:
a shell comprising a posterior cephalic portion, a posterior caudal portion, an anterior cephalic portion, and an anterior caudal portion;
an anchor coupled within the shell and coupled directly and fixedly to the posterior caudal portion and the anterior caudal portion, wherein the anchor comprises a recess therein; and;
a fluid comprised in the recess and the shell;
wherein the anchor prevents rotation of the breast implant;
wherein the anchor prevents flipping of the breast implant;
wherein an outer surface of the shell is non-textured;
wherein the breast implant comprises an anatomical shape; and
wherein the fluid is directly in contact with an entire inner surface of the anterior cephalic portion of the shell.

8. The breast implant of claim 7, wherein the anchor is configured to prevent buckling of the breast implant.

9. The breast implant of claim 7, wherein the anchor forms a lip at an interface between the anterior caudal portion and the anterior cephalic portion.

10. The breast implant of claim 7, wherein the anchor extends around a perimeter of a posterior portion of the shell, wherein the posterior portion comprises the posterior cephalic portion and the posterior caudal portion.

11. The breast implant of claim 7, wherein an entirety of an inner surface of the anterior caudal portion and the posterior caudal portion is directly and fixedly coupled to the anchor.

12. The breast implant of claim 7, wherein the anchor extends from a base of a posterior portion to a top of the posterior portion, wherein the posterior portion comprises the posterior cephalic portion and the posterior caudal portion.

13. The breast implant of claim 7, wherein the anchor and the shell are continuously formed from a same material.

14. A breast implant comprising:
a shell comprising a posterior portion and an anterior portion; and
an anchor coupled within the shell and coupled directly and fixedly to an entire interface on an inner surface of the shell between the posterior portion and the anterior portion;
wherein the anchor prevents flipping of the breast implant; and
wherein an outer surface of the shell is non-textured; and
wherein the breast implant is a round implant.

15. The breast implant of claim 14, wherein the anchor forms a cross directly and fixedly coupled to the anterior portion.

16. The breast implant of claim 14, wherein the anchor is directly and fixedly coupled to an entire inner surface of the posterior portion.

17. The breast implant of claim 14, wherein the anchor comprises a solid implant comprising a recess formed therein, wherein the recess is filled with a fluid medium.

18. The breast implant of claim 14, wherein the anchor and the shell are continuously formed from a same material.

* * * * *